US00RE36576E

United States Patent [19]

Baikoff et al.

[11] E Patent Number: Re. 36,576

[45] Reissued Date of Patent: Feb. 15, 2000

[54] INTRAOCULAR IMPLANT FOR CORRECTION OF MYOPIA

[75] Inventors: Georges Baikoff, Marseilles; Philippe Subrin, Domarin, both of France

[73] Assignee: Bausch & Lomb Surgical, Inc., Claremont, Calif.

[21] Appl. No.: 08/627,494

[22] Filed: Apr. 4, 1996

Related U.S. Patent Documents

Reissue of:

[64] Patent No.: 5,300,117
Issued: Apr. 5, 1994
Appl. No.: 07/749,167
Filed: Aug. 23, 1991

[30] Foreign Application Priority Data

Sep. 4, 1990 [FR] France ..... 90 11236

[51] Int. Cl.[7] ..... A61F 2/16
[52] U.S. Cl. ..... 623/6
[58] Field of Search ..... 623/6

[56] References Cited

U.S. PATENT DOCUMENTS 4,666,446 5/1987 Koziol et al. ..... 623/6
4,676,792 6/1987 Praeger ..... 623/6
4,769,035 9/1988 Kelman ..... 623/6

FOREIGN PATENT DOCUMENTS 0346245 12/1989 European Pat. Off. ..... 623/6
8906115 7/1989 WIPO ..... 623/6

*Primary Examiner*—David H. Willse
*Attorney, Agent, or Firm*—Banner & Witcoff, Ltd; Rita D. Vacca

[57] ABSTRACT

An intraocular implant includes an optic part consisting of a central diverging lens of minus optical power, whose thickness increases radially from its optical center, and a peripheral edge shaped in the manner of a converging lens, and a haptic part for supporting the optic part, on each side of the latter, wherein the implant has the function of correcting myopia and is designed to be arranged in the anterior chamber of the eye, without ablation of the crystalline lens, the central diverging lens being a corrective lens, and the peripheral converging lens being a lens for focusing the peripheral light in front of the retina.

3 Claims, 2 Drawing Sheets

INTRAOCULAR IMPLANT FOR CORRECTION OF MYOPIA

Matter enclosed in heavy brackets [ ] appears in the original patent but forms no part of this reissue specification; matter printed in italics indicates the additions made by reissue.

BACKGROUND OF THE INVENTION

The present invention relates to an intraocular implant intended to be inserted in the anterior chamber of the eye, by ophthalmic surgery, in order to correct the patient's myopia without ablation of the crystalline lens.

DESCRIPTION OF THE PRIOR ART

The document EP-A-0 346 245 describes and proposes an implant of the type defined hereinabove, consisting:

of an optic part, essentially comprising a diverging corrective lens of minus optical power, for example a biconcave lens, and whose thickness consequently increases generally from its optical axis toward its periphery, the latter then having an edge of relatively large thickness;

and of a haptic part comprising, for example, two support loops arranged opposite each other, for supporting the optic part, on both sides of the latter, in the anterior chamber of the corrected eye.

In accordance with the established terminology in the technical field of the present invention, the expression "optic" or "optic part" designates in a general manner that part of the implant penetrated by the light rays passing through the pupil, whatever the degree of dilation of the latter. All or part of this optic part can be occupied by the actual corrective lens itself, of an optical power appropriate to the desired correction.

As regards the expression "haptic" or "haptic part", this designates that part of the implant which essentially has no role or function with regard to the light rays passing through the pupil, and which ensures in a suitable manner the support, the deployment, and the positioning of the optic part in the anatomical seat of the eye intended to receive it.

As is known, the haptic part and the optic part can be separate, or can be obtained in monobloc fashion made from one and the same material, for example a suitable plastic material.

According to the document EP-A-0 346 245, the optic part coincides almost completely with the corrective lens, which can in this case have a relatively large diameter [or radius], at least equal to 4.5 mm, more effectively covering the visual field of the pupil.

This being the case, accumulated experience on the degree of acceptance by the patient of such implants has revealed the following difficulty.

In the case of dim light received by the eye of the patient, the latter perceives a diffuse luminous halo interfering with the distinct perception of an image, notwithstanding the satisfactory correction obtained with the optic part of the implant.

The inventors therefore carried out optical analysis of the fault thus noted, and detailed hereinbelow, in order to identify the origin of the above-mentioned halo; and it is this origin, duly recognized, which forms the basis of the present invention.

In dim light, for example in night vision, the patient's pupil is dilated in a relatively large and substantially circular section. This section may be greater than the surface of the optic part of the implant concentric or coaxial with the optical axis of the eye, so that there then exists in the anterior chamber of the eye an annular gap which is not covered by this same optic part. A ray or peripheral light can pass through this gap and reach the iris of the patient's eye directly, that is to say without absorption or passage through the optic part of the implant.

A small proportion of this peripheral ray is reflected on the relatively thick edge of the optic part, acting as a mirror, and arrives in a diffuse manner on the retina.

A larger part of the peripheral ray passes directly into the iris and arrives unfocused on the retina, that is to say focused in front of the retina, given the myopia of the patient.

In short, on account of this peripheral ray, the retina receives a plurality of superimposed spots corresponding to images defocused in different ways and together generating a luminous halo which, although of low intensity, nevertheless "parasitizes" to some extent the image focused on the retina, obtained with the corrective lens.

It does not appear to be possible to increase the diameter of the optic part, and therefore of the corrective lens, since this leads immediately to an increase in the thickness of the edge of this same optic part. Such an increase would risk causing contacts between implant and corneal endothelium, the depth of the anterior chamber of the phakoid eye being relatively reduced.

On the basis of this analysis, the aim of the present invention is to overcome or control this peripheral ray, at the edge of the corrective lens, so as to transform it on the retina into a luminous signal compatible with the image arising from the corrective lens.

SUMMARY OF THE INVENTION

According to the present invention, this result is achieved by combining the following three design choices:

1) the radial extension of the corrective lens, from its center or from its optical axis, is limited by a circle with a [radius] *diameter* of between 3.5 and 4.5 mm; a corrective lens is thus chosen which is inscribed within a circle having a diameter relatively smaller than that or those envisaged in the document EP-A-0 346 345;

2) the radial extension of the optic part, from its center, or from the optical axis of the corrective lens, is increased to a circle with a [radius] *diameter* of between 4.8 and 6.5 mm; an optic part is thus chosen which is inscribed within a circle having a diameter relatively greater than that or those envisaged in the document EP-A-0 346 245, as a result of which there is formed or kept clear, around the corrective lens, an edge penetrated by the peripheral light which may pass through the pupil;

3) this peripheral edge is shaped in the manner of a converging defocusing lens, of plus power in the range between 20 and 60 diopters, for focusing the peripheral light in front of the retina.

By virtue of the invention, the light or the peripheral ray discussed hereinabove is controlled, that is to say focused, on a zone of limited axial extension, well in front of the retina, as a result of which the latter receives a relatively homogeneous and uniform luminous spot (of low luminous intensity because it is well focused) surrounding the image focused by the corrective lens, in a retinal zone of low visual acuity. Experience shows that, in these conditions, it is then much easier for the patient's eye to discriminate or distinguish the corrected image.

The dimensions chosen according to the invention make it possible to situate the converging focusing edge in a ring with an inner [radius] *diameter* equal to 3.5 mm and an outer [radius] *diameter* equal to 6.5 mm. The choice of the effective dimensions of the focusing edge, like those of the implant, depends in part on the myopia to be corrected and on the configuration of the patient's eye. This being the case, experience has shown that, as regards this focusing edge, it is difficult to go below 3.5 mm without affecting the correction afforded by the lens, or to go above 6.5 mm without risking contact between implant and corneal endothelium.

As far as the optical power of the focusing edge is concerned, experience has also shown that, below 20 diopters, the focusing point of the peripheral ray comes too close to the retina, so that the luminous spot becomes perceptible by the retina. And, above 60 diopters, the radius of curvature of the focusing edge becomes difficult to match with that of the lens and, as mentioned above, the thickening of the edge of the lens increases the risk of contact with the corneal endothelium.

According to the document US-C-4 666 446, and more specifically the embodiment described with reference to FIGS. 13 to 15, and according to the document WO-A-89 06115, and more specifically to the embodiment shown in FIGS. 5 and 6, there is proposed and described, with a completely different function and in another application, an intraocular implant comprising:

- an optic part consisting of a central diverging lens of minus optical power, whose thickness increases radially from its optical center, and a peripheral edge shaped in the manner of a converging lens
- and a haptic part for supporting the optic part, on each side of the latter.

Such an intraocular implant, prescribed and used in order to rectify macular degeneration, is arranged in the posterior chamber of the eye, and consequently behind the pupil, after ablation of the crystalline lens, and thus as a replacement for the latter. The function of this implant is to afford the patient two types of vision, namely:

- solely by means of the peripheral converging lens of the optic part, a non-magnified vision, with an unlimited angular field,
- by means of the central diverging lens of the optic part, and in combination with converging glasses worn by the patient, and in the manner of a galilean telescope with the diverging part in the eye and the converging part outside the eye, a magnified vision, but with a limited angular field.

The implants described in the documents US-C-4 666 446 and WO-A-89 06115 are therefore totally different from those according to the present invention, in terms of their function and their ophthalmic application and use.

More precisely, the implants according to the invention differ from those described in this prior art in that their function is to correct myopia, they are designed to be arranged in the anterior chamber of the eye, without ablation of the crystalline lens, and in that, in these conditions, the central diverging lens is a corrective lens, and the converging lens is a lens for focusing the peripheral light in front of the retina.

According to the present invention, the optic part can have any suitable shape, for example circular, the preceding definition specifying only the outer limit within which this optic part must be inscribed. The same applies to the corrective lens, the preceding definition specifying only the outer limit within which this lens must be inscribed.

Moreover, in a manner already known per se, the corrective lens can be made up of at least two partial lenses, still diverging, but of respectively different optical or focal powers, these partial lenses being arranged in the optic part in any suitable manner, in particular diametrically opposed, concentric, etc. In the case of a plurality of partial lenses, the variation in their respective minus optical powers can be obtained in a virtually continuous manner, such that the corrective lens has an anterior face and/or a posterior face of regular profile. The corrective lens and the focusing edge can be made from different materials, depending on the desired refractive index.

The present invention additionally affords the following crucial advantages.

Compared to an implant according to the document EP-A-0 346 245, for the same optical power of the corrective lens, the optic part of the implant is situated at a distance from the endothelium of the eye at least equal to 0.5 mm. This results entirely or partly from the preceding design choices:

- by limiting the radial extension of the corrective lens, the thickness of its edge is limited, while at the same time limiting its height in the anterior chamber
- the peripheral focusing edge has in section a converging profile, which limits the radial extension of the optic part.

All this favors both the correct deployment of the implant in the anterior chamber of the eye, that is to say without damaging the endothelium, and a position of the implant free from any contact with the endothelium during the activity of the patient bearing the implant Furthermore, the converging shape of the focusing edge confers upon the optic part a shape which is much more anatomical relative to the anterior chamber of the eye. This makes it possible to compensate to some extent for the shape of the corrective lens, opposed to that of this same chamber.

BRIEF DESCRIPTION OF THE DRAWINGS

The present invention is now described with reference to the attached drawings, in which.

DESCRIPTION OF THE PREFERRED EMBODIMENTS

Figure 1:
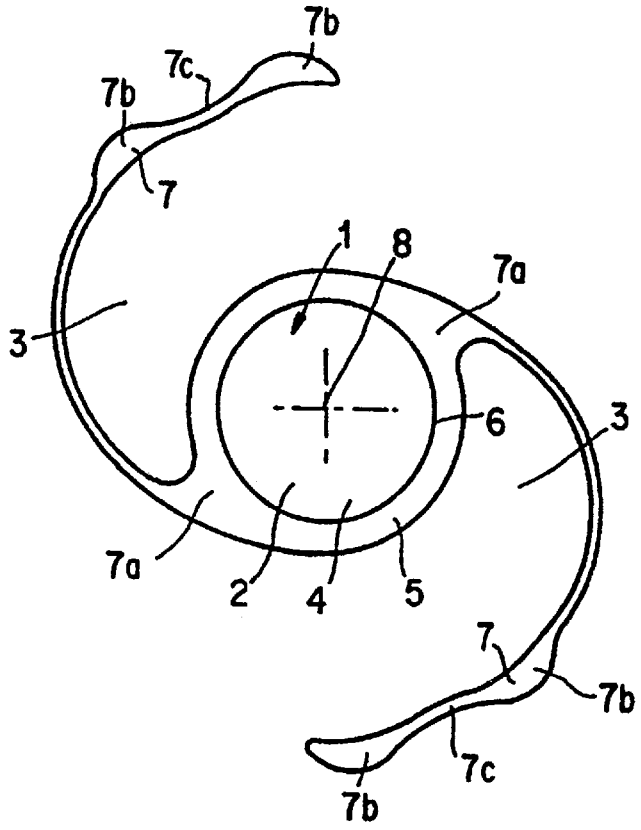
FIG. 1 shows a front view of an intraocular implant according to the present invention.
Figure 2:
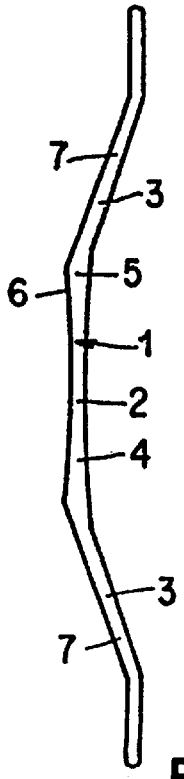
FIG. 2 shows a side view of the same implant.

According to FIGS. 1 and 2, the implant 1 according to the invention comprises in a generic manner an optic part 2 and a haptic part 3. The optic part 2 comprises, on the one hand, a diverging lens 4 for correction of the myopia, which lens is biconcave and consequently of minus optical power (between −5 and −30 diopters), and of circular profile, and, on the other hand, an annular edge 5 shaped in the manner of meniscus or converging lens, and consequently having convex anterior face, forming a zone of inflexion 6 with the concave anterior face of the lens 4, and a concave posterior face, situated approximately in the extension of the concave posterior face of the same lens 4. As regards the haptic part 3, it consists of two loops 7 situated opposite each other, each one comprising at one end an attachment zone 7a, on the focusing edge 5, and at the other free end an integrated support zone, consisting of two contact pads 7b spaced apart from one another. As is shown in FIG. 1, the two loops 7 are curved uniformly toward the optic part 2, from their attachment zones 7a to their support zones 7c, in the same centripetal direction, relative to the center or optical axis 8 of the implant.

As has already been mentioned, the focusing edge 5, the corrective lens 4 and the haptic part 3 can be obtained in a monobloc fashion made from one and the same material, for example of PMMA (polymethyl methacrylate). It is also possible to use other materials having a relatively high refractive index, for example between 1.65 and 1.75, in particular polysulfone, making it possible, for the same optical corrective power, to limit still further the thickness of the lens 4, and therefore its height or radial extension.

The dimensions and other geometrical parameters of the implant are generally adapted, on the one hand, to the myopia to be corrected and, on the other hand, to the anatomy of the eye receiving the implant. This being the case, as has already been mentioned, the radial extension of the central corrective lens 4 is limited by a circle with a [radius] *diameter* of between 3.5 and 4.5 mm, whilst the radial extension of the optic part 2 or peripheral edge 5 is increased up to a circle with a [radius] *diameter* of between 4.8 and 6.5 mm. As is shown in FIG. 2, a portion of the haptic part 3, and more specifically a branch 3 of the loops, has an angle, relative to the plane of the optic part 2, of between 20° and 25°; as is shown with reference to FIG. 3, this makes it possible to maintain or position the implant at a distance from the cornea, the pupil and the crystalline lens.

Figure 3:
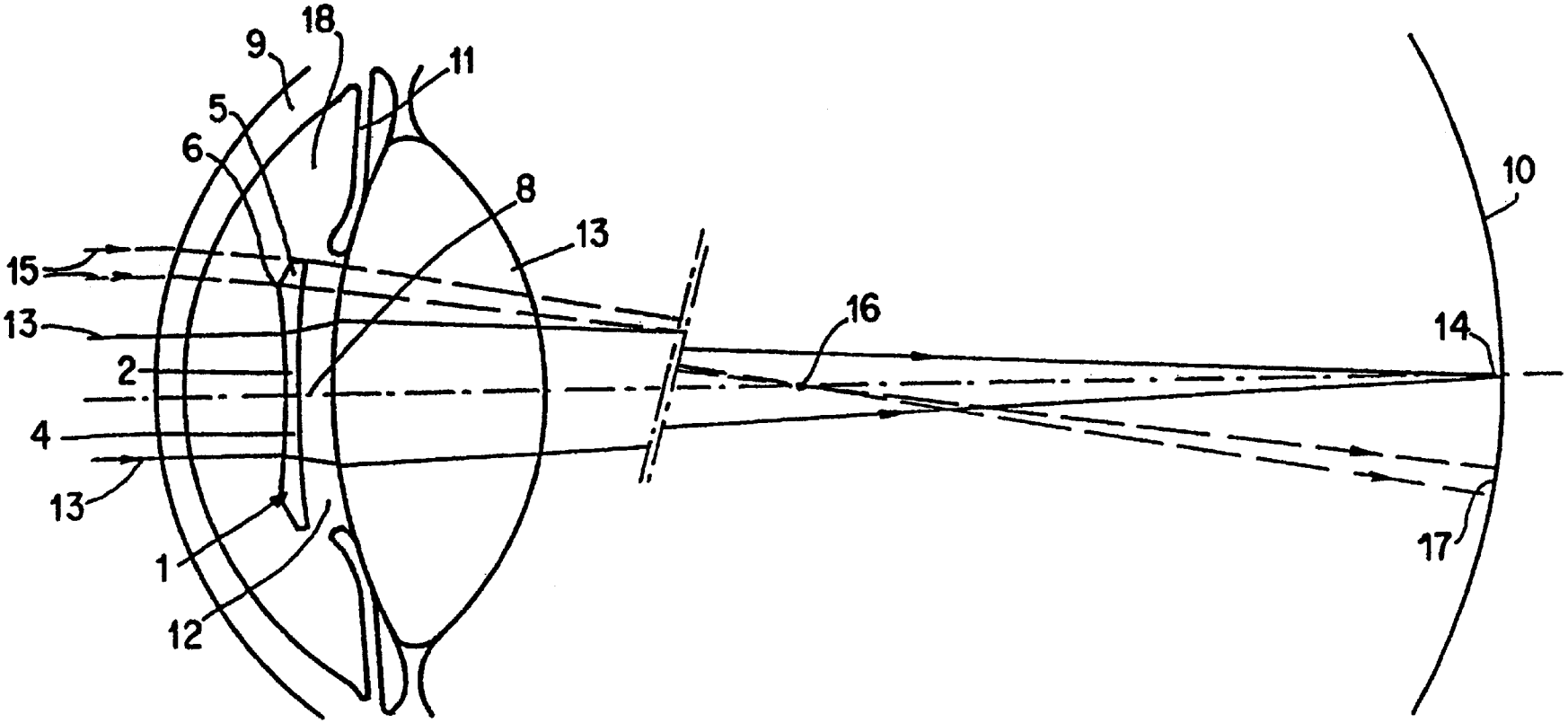
FIG. 3 shows diagrammatically the optical correction obtained with an implant according to the present invention.

The eye receiving the implant and comprising the cornea 9, the retina 10, the iris 11, the pupil 12 and the crystalline lens 13 has been shown diagrammatically in FIG. 3. The ophthalmic operation results in the deployment of the implant 1 in accordance with the optical axis of the eye, coinciding with that of the optic part 2, or lens 4. Taking into account the correction afforded by the lens 4, a ray 13 passing through the center of the pupil 12 is focused at 14 on the retina 10. In dim light, for example in night vision, the iris 11 is caused to retract, as shown in FIG. 3; in this configuration, the optic part 2 of the implant still covers the pupil 12, by virtue of the design choices according to the invention. Still in this configuration, a peripheral ray 15 is defocused relative to the retina 10 and more precisely focused at the point 16, in front of the retina 10, in such a way that a spot 17 of low luminous intensity is obtained on the retina 10. Experience shows that the corrected image 14 can be discriminated or distinguished much better by the eye, compared to the spot 17, so that the patient tolerates much better an implant according to the present invention.

We claim:

1. An intraocular implant, comprising an optic part consisting essentially of a central diverging lens of minus optical power, whose thickness increases radially from its optical center, and a peripheral edge shaped in the manner of a converging lens, and a haptic part for supporting said optic part, on each side of the optic part, wherein said implant has the function of correcting myopia and is designed to be arranged in the anterior chamber of the eye, without ablation of the crystalline lens, the central diverging lens being a corrective lens, and the peripheral converging lens being a lens for focusing peripheral light in front of the retina, wherein, in combination, radial extension of the central diverging lens is limited by a circle with a [radius] *diameter* of between 3.5 and 4.5 mm, radial extension of the peripheral converging lens is increased to a circle with a [radius] *diameter* of between 4.8 and 6.5 mm, in order to cover the retina in dim light, and said peripheral converging lens has a plus power in a range between 20 and 60 diopters.

2. The implant as claimed in claim 1, wherein at least the central diverging lens is made of a material having a refractive index between 1.65 and 1.75.

3. The implant as claimed in claim 2, wherein said material is polysulfone.

* * * * *